US008524905B2

(12) United States Patent
Gharat et al.

(10) Patent No.: US 8,524,905 B2
(45) Date of Patent: Sep. 3, 2013

(54) PROCESSES FOR PREPARING 6-(DIFLUOROMETHOXY)[1]BENZOFURO[3,2-C]PYRIDINE-9-CARBALDEHYDE, A NOVEL INTERMEDIATE FOR THE SYNTHESIS OF PDE IV INHIBITORS

(75) Inventors: Laxmikant Atmaram Gharat, Thane (IN); Jitendra Maganbhai Gajera, Navi Mumbai (IN); Sandip Damodar Patil, Navi Mumbai (IN); Suresh M. Kadam, Thane(w) Mumbai (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 497 days.

(21) Appl. No.: 12/601,245

(22) PCT Filed: May 21, 2008

(86) PCT No.: PCT/IB2008/001272
§ 371 (c)(1),
(2), (4) Date: Nov. 20, 2009

(87) PCT Pub. No.: WO2008/142542
PCT Pub. Date: Nov. 27, 2008

(65) Prior Publication Data
US 2010/0168151 A1    Jul. 1, 2010

Related U.S. Application Data

(60) Provisional application No. 60/941,816, filed on Jun. 4, 2007.

(30) Foreign Application Priority Data

May 22, 2007  (IN) ............................ 955/MUM/2007

(51) Int. Cl.
*C07D 491/00*    (2006.01)

(52) U.S. Cl.
USPC .......................................................... 546/89

(58) Field of Classification Search
USPC .......................................................... 546/89
See application file for complete search history.

(56) References Cited

U.S. PATENT DOCUMENTS 7,943,634 B2 *  5/2011  Gharat et al. .................. 514/291

FOREIGN PATENT DOCUMENTS

| WO | WO-2004089940 A1 | 10/2004 |
| WO | WO-2006040652 A2 | 4/2006 |
| WO | WO-2006064355 A2 | 6/2006 |

OTHER PUBLICATIONS

O'Brien et al., Critical Reviews in Toxicology, Aug. 1, 2005.*
Rogers, D.F., Giembycz, M.A., *Trends Pharmacol. Sci.* 1998; 19:160-164.
Barnes, P.J., *Trends Pharmacol. Sci.* 1998; 19:415-423.
Engelhard M., Merrifield R. B., *J. Am. Chem. Soc.* 1978; 100, 3559-3563.
Julemon, et al., Spectral and Crystallographic Study of Pyridinic Analogues of Nimesulide: Determination of the Active Form of Methanesulfonamides as COX-2 Selective Inhibitors, J. Med. Chem. 2002, 45, 5182-5185.
International Search Report for PCT/IB2008/001272 dated Feb. 3, 2009.

* cited by examiner

*Primary Examiner* — Nizal Chandrakumar
(74) *Attorney, Agent, or Firm* — Blank Rome LLP

(57)  ABSTRACT

The present invention relates to novel processes for preparing 6-(difluoromethoxy)[1]benzofuro[3,2-c]pyridine-9-carbaldehyde, which is a novel and useful intermediate for preparing compounds with PDE4 inhibitory activity, such as 3,5-dichloro-4-(6-difluoromethoxybenzo[4,5]furo[3,2-c]pyridin-9-ylcarboxamido)-1-pyridiniumolate.

5 Claims, No Drawings

PROCESSES FOR PREPARING 6-(DIFLUOROMETHOXY)[1]BENZOFURO[3,2-C]PYRIDINE-9-CARBALDEHYDE, A NOVEL INTERMEDIATE FOR THE SYNTHESIS OF PDE IV INHIBITORS

This is the U.S. National Phase Application under 35 U.S.C. §371 of International Application no. PCT/IB2008/001272, filed May 21, 2008, which claims priority to Indian Patent Application No. 955/MUM/2007, filed May 22, 2007, and U.S. provisional Application No. 60/941,816, filed Jun. 4, 2007, all of which are incorporated by reference in their entireties. The International Application was published in English on Nov. 27, 2008 as WO/2008/142542 under PCT Article 21 (2).

FIELD OF THE INVENTION

The present invention relates to novel processes for preparing 6-(difluoromethoxy)[1]benzofuro[3,2-c]pyridine-9-carbaldehyde, which is a novel and useful intermediate for preparing compounds with PDE4 inhibitory activity, such as 3,5-dichloro-4-(6-difluoromethoxybenzo[4,5]furo[3,2-c]pyridin-9-ylcarboxamido)-1-pyridiniumolate and its sodium salt.

BACKGROUND OF THE INVENTION

The phosphodiesterase enzymes play an integral role in cell signaling mechanisms by hydrolyzing cAMP and cGMP to their inactive 5' forms. Inhibition of PDE enzymes results in an elevation of cAMP and/or cGMP levels and alters intracellular responses to extracellular signals by affecting the processes mediated by cyclic nucleotides. It has been demonstrated that increasing cAMP levels within these cells results in suppression of cell activation, which in turn inhibits the production and release of pro-inflammatory cytokines such as TNF-α. Since eosinophils are believed to be a critical pro-inflammatory target for asthma, identification of the expression of the PDE4 gene family in eosinophils led to PDE4 as a potential therapeutic target for asthma [Rogers, D. F., Giembycz, M. A., *Trends Pharmacol. Sci.*, 19, 160-164, (1998); Barnes, P. J., *Trends Pharmacol. Sci.*, 19, 415-423, (1998)].

PCT Publication No. WO 2006/064355 (WO '355) discloses PDE4 inhibitors of the formula

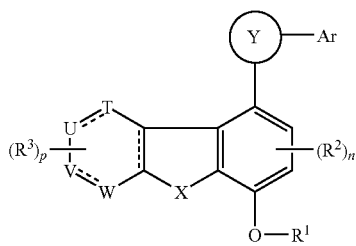

Formula I including, 3,5-dichloro-4-(6-difluoromethoxybenzo[4,5]furo[3,2-c]pyridin-9-ylcarboxamido)-1-pyridiniumolate. 6-(difluoromethoxy)[1]benzofuro[3,2-c]pyridine-9-carbaldehyde, is an intermediate useful for preparing compounds with PDE4 inhibitory activity such as 3,5-dichloro-4-(6-difluoromethoxy benzo[4,5]furo[3,2-c]pyridin-9-ylcarboxamido)-1-pyridiniumolate.

WO '355 discloses processes for preparing these compounds. However, these processes are not suitable for commercial scale production of the compounds as they require hazardous reagents (such as 4-methylbenzenethiol, tin(IV) chloride and dichloromethylmethyl ether), have low yield, and produce the compounds in low purity.

The present invention provides alternative novel processes, which is economical, convenient, efficient and easily scalable. Furthermore, the yields and purity of intermediates, including 6-(difluoromethoxy)[1]benzofuro[3,2-c]pyridine-9-carbaldehyde, and final products are high.

SUMMARY OF THE INVENTION

The present invention provides novel processes for preparing 6-(difluoromethoxy) [1]benzofuro[3,2-c]pyridine-9-carbaldehyde, which is a novel intermediate useful for preparing compounds with PDE4 inhibitory activity. The present invention overcomes the disadvantages of schemes described in WO '355 by reducing the number of steps and by avoiding the use of 4-methylbenzenethiol, tin(IV)chloride and dichloromethylmethyl ether. The invention further provides a process for preparing a PDE4 inhibitor such as 3,5-dichloro-4-(6-difluoromethoxybenzo[4,5]furo[3,2-c]pyridin-9-ylcarboxamido)-1-pyridiniumolate.

One embodiment of the present invention is a process for preparing a compound of formula (10):

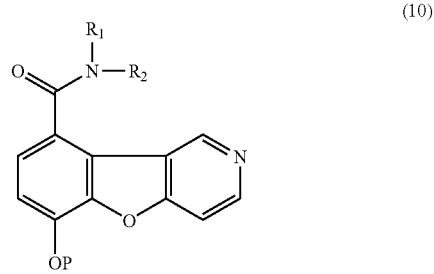

(10)

or an N-oxide or a pharmaceutically acceptable salt thereof, wherein:

$R_1$ and $R_2$ are independently hydrogen, alkyl, aryl, heteroaryl or heterocyclyl, or $R_1$ and $R_2$ together, with the nitrogen atom to which they are attached, form a 3-7 membered heterocyclyl optionally containing one or more heteroatoms selected from O, S and N; and P is selected from an optionally substituted benzyl, alkyl, halogenated alkyl, cycloalkyl, cycloalkylalkyl, silyl, allyl, propargyl, tetrahydropyran, alkoxyalkyl and silyloxyalkyl. The method includes the steps of:

(i) converting a compound of the formula (5) to a compound of formula (6)

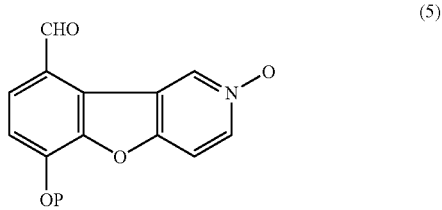

(5)

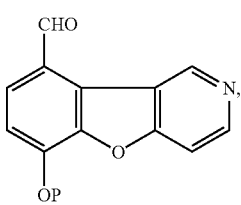

(6)

and (ii) converting a compound of formula (6) to a compound of formula (10) or an N-oxide or a pharmaceutically acceptable salt thereof. A preferred N-oxide of the compound of formula (10) is 3,5-dichloro-4-(6-difluoromethoxybenzo[4,5]furo[3,2-c]pyridin-9-ylcarboxamido)-1-pyridiniumolate.

Another embodiment of the present invention is a process for preparing a compound of formula (6)

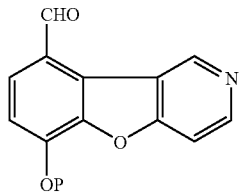

(6)

wherein P is as defined above. Preferably, P is cyclopentyl or $CHF_2$. For instance, the compound of formula (6) can be 6-(difluoromethoxy)[1]benzofuro[3,2-e]pyridine-9-carbaldehyde. The process includes one or more of the following steps of:

(a) reacting the hydroxy group of a compound of formula (2) with 3-bromo-4-chloropyridine-N-oxide of formula (3)

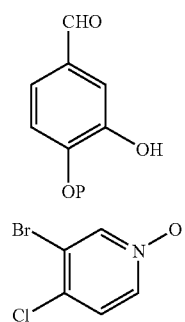

(2)

(3)

to form a compound of formula (4)

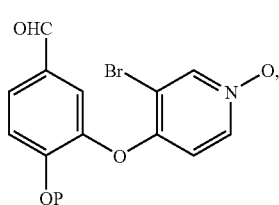

(4)

(b) cyclizing the compound of formula (4) to form a compound of formula (5)

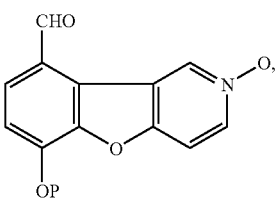

(5)

and (c) converting the compound of formula (5) into a compound of formula (6)

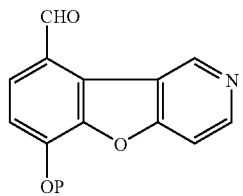

(6)

The reaction in step (a) can be performed by reacting the compound of formula (2) with a compound of formula (3). Preferably, this reaction is performed in the presence of one or more metal halides, metal hydrides (such as sodium hydride), metal alkoxides (such as potassium t-butoxide) and optionally in one or more solvents. Suitable metal halides include, but are not limited to, potassium fluoride, cesium fluoride, sodium fluoride, and mixtures thereof. Preferably, the reaction is performed in the presence of potassium fluoride. The reaction is also preferably carried out in one or more high boiling solvents (i.e., a solvent with an initial boiling point above 140° C.) such as dimethylsulfoxide, dimethylformamide, N,N-dimethylacetamide, N-methylpyrrolidone or a mixture thereof. In one preferred embodiment, the solvent is selected from dimethylsulfoxide and dimethylformamide.

The cyclization in step (b) can be performed by reacting the compound of formula (4) with one or more cyclizing agents. Suitable cyclizing agents include, but are not limited to, palladium reagents, such as palladium acetate (monomer or trimer), palladium complexes, and palladium halides, and any mixture thereof. Preferably, this reaction is performed in the presence of in one or more high boiling solvents, such as dimethylformamide, dimethylsulfoxide, N,N-dimethylaniline, N-methylpyrrolidine or any mixture thereof. This reaction is also preferably carried out in the presence of a base such as sodium acetate, sodium carbonate, triethylamine, or any mixture thereof.

The conversion in step (c) can be performed by reacting the compound of formula (5) under reductive conditions with one or more metal powders and/or one or more organic acids. Suitable metal powders include, but are not limited to, iron powder, zinc powder, and any mixture thereof. Suitable organic acids include, but are not limited to, acetic acid, trifluoroacetic acid, propionic acid, and any mixture thereof.

Alternatively, a compound of formula (6), where P is $CHF_2$, can be formed by (c)(i) deprotecting a compound of formula (5) (where, for example, P is cycloalkyl, such as cyclopentyl) to form a compound of formula (7)

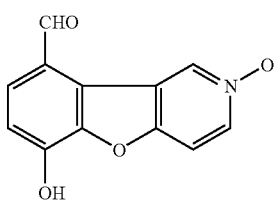

(7)

and (c)(ii) reacting the compound of formula (7) with, for example, one or more difluoromethylating agents. In one embodiment, P in the compound of formula (5) is not $CHF_2$.

The deprotection step (c)(i) can be performed by reacting the compound of formula (5) with one or more deprotecting agents. Preferably, this reaction is performed in the presence of one or more deprotecting agents and optionally in the presence of one or more metal hydroxides. Suitable deprotecting agents include, but are not limited to, hydrochloric acid (e.g., aqueous hydrochloric acid), hydrobromic acid (e.g., hydrobromic acid in acetic acid or aqueous hydrobromic acid), boron tribromide, aluminium chloride, sodium alkyl or aryl thiolate, tetra-n-butylammonium fluoride, hydrogenating catalysts (e.g., palladium on carbon, rhodium on carbon, platinum black, palladium chloride, platinum oxide, ruthenium or a mixture thereof), or any mixture thereof. A preferred deprotecting agent is aqueous hydrobromic acid. Suitable metal hydroxides include, but are not limited to, alkali metal hydroxides (such as sodium hydroxide, lithium hydroxide or potassium hydroxide), alkaline earth metal hydroxides (such as calcium hydroxide or magnesium hydroxide), and any mixture thereof.

The difluoromethylation step (c)(ii) can be performed by reacting the compound of formula (7) with of one or more difluoromethylating agents in one or more solvents. Suitable difluoromethylating agents include, but are not limited to, chlorodifluoromethane, sodium chlorodifluoroacetate and mixtures thereof. Suitable solvents include, but are not limited to, ethers (e.g., diethyl ether, tetrahydrofuran and dioxane), aliphatic hydrocarbons (e.g., hexane and heptane), aromatic hydrocarbons (e.g., toluene and xylene), halogenated solvents (e.g., dichloromethane, dibromomethane, chloroform, and carbon tetrachloride), aprotic polar solvents (e.g., dimethylformamide, dimethylsulfoxide, N,N-dimethyl aniline and N-methyl pyrrolidine), protic polar solvents (e.g., methanol, ethanol, isopropanol, butanol and isobutanol), and any mixture thereof.

The compound of formula (6) can be converted into a compound of formula (10)

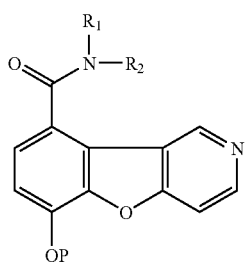

(10)

or an N-oxide or a pharmaceutically acceptable salt thereof, wherein:

$R_1$ and $R_2$ are as defined above. Preferably, $R_1$ is hydrogen and $R_2$ is 3,5-dichloro-4-pyridinyl or 3,5-dichloro-4-pyridinyl-N-oxide.

For example, the compound of formula (6) (when P is $CHF_2$) can be converted into the compound of formula (10) by (d) oxidizing the compound of formula (6) with one or more oxidizing agents to form a compound of formula (8)

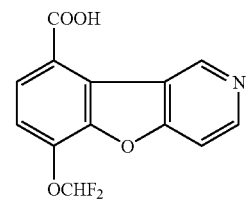

(8)

(e) reacting the compound of formula (8) with 4-nitro phenol to form a compound of formula (9),

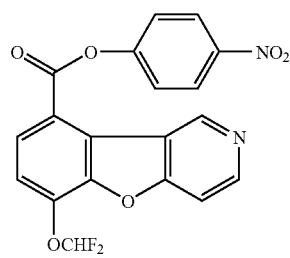

(9)

and f) reacting the compound of formula (9) with an amine of the formula $NHR_1R_2$ (where $R_1$ and $R_2$ are as defined above) to form a compound of formula (10), which is optionally converted into an N-oxide or pharmaceutically acceptable salt thereof.

Another embodiment is a process for preparing a compound of formula (4)

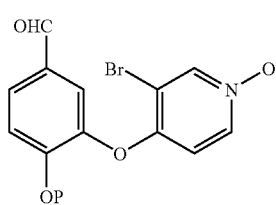

(4)

wherein P is selected from an optionally substituted benzyl, alkyl (e.g., halogenated alkyl), cycloalkyl, cycloalkylalkyl, silyl, allyl, propargyl, tetrahydropyran, alkoxyalkyl or siloxyalkyl. Preferably, P is cyclopentyl or $CHF_2$. The process involves reacting the compound of formula (2) with the compound of formula (3). The reaction can be performed in the presence of one or more metal halides, metal hydrides, or metal alkoxides, optionally in one or more solvents. Any of the aforementioned metal halides, metal hydrides, or metal alkoxides may be used. For example, the reaction may be performed in potassium fluoride and dimethylsulfoxide or sodium hydride and dimethylformamide. The compound of formula (4) can be converted to 3,5-dichloro-4-(6-difluoromethoxybenzo[4,5]furo[3,2-c]pyri din-9-ylcarboxamido)-1-pyridiniumolate, a compound of formula (10) or an N-oxide or a pharmaceutically acceptable salt thereof.

Yet another embodiment is a process for preparing a compound of the formula (5)

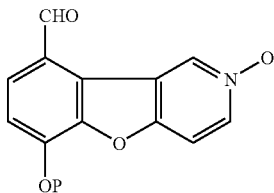
(5)

wherein P is as defined above. Preferably, P is cyclopentyl or CHF$_2$. The process involves cyclizing a compound of formula (4). The cyclization can be performed by reacting the compound of formula (4) with one or more cyclizing agents, such as those mentioned above, optionally in the presence of a base. For example, the reaction can be performed in the presence of palladium acetate (monomer or trimer) and a base, such as sodium acetate. The cyclization is optionally carried out in one or more high boiling solvents such as dimethylformamide. The compound of formula (5) can be converted to 3,5-dichloro-4-(6-difluoromethoxybenzo[4,5]furo[3,2-c]pyridin-9-ylcarboxamido)-1-pyridiniumolate, a compound of formula (10), an N-oxide thereof, or a pharmaceutically acceptable salt thereof.

Yet another embodiment is a process for preparing a compound of the formula (7)

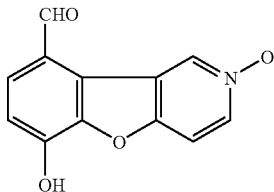
(7)

by deprotecting the compound of formula (5). The deprotection can be performed by reacting the compound of formula (5) with one or more deprotecting agents as discussed above. For instance, the deprotection can be performed in the presence of aqueous hydrobromic acid. The compound of formula (7) can be converted to 3,5-dichloro-4-(6-difluoromethoxybenzo[4,5]furo[3,2-c]pyridin-9-ylcarboxamido)-1-pyridiniumolate, a compound of formula (10), an N-oxide thereof, or a pharmaceutically acceptable salt thereof.

Yet another embodiment is a pharmaceutical composition comprising:
(a) a compound of the formula (10)

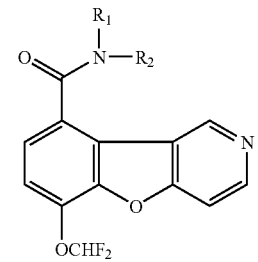
(10)

an N-oxide thereof or pharmaceutically acceptable salt thereof, wherein R$_1$ and R$_2$ are as defined above; and (b) a compound selected from

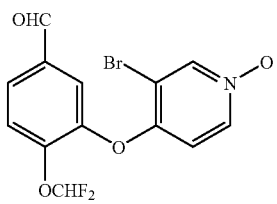
(a)

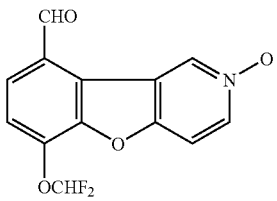
(b)

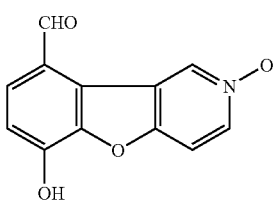
(c)

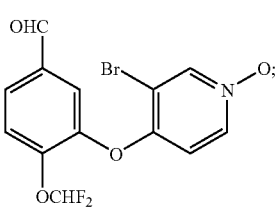
(7)

or a salt thereof. Preferably, the compound in component (b) is present in an amount up to 1% by weight (and more preferably up to 0.1%), based upon 100% total weight of components (a) and (b). The compound in component (a), i.e., the active component, is preferably present in an amount up to 95% (and more preferably up to 98, 99 or 99.9%), based upon 100% total weight of components (a) and (b).

Yet another embodiment is a compound selected from:

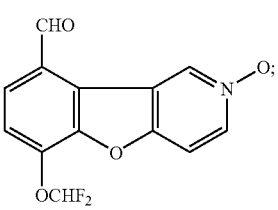
(a)

(b)

-continued (c)

Structure: benzofuran-pyridine with CHO and OCHF₂ substituents (7)

Structure: benzofuran-pyridine N-oxide with CHO and OH substituents or a salt thereof.

Processes described herein can include one or more of the following embodiments.

In one embodiment, the metal halide in step (a) is selected from potassium fluoride, cesium fluoride, sodium fluoride, and mixtures thereof.

In another embodiment, the metal hydride in step (a) is selected from sodium hydride and potassium hydride.

In yet another embodiment, the metal alkoxide in step (a) is selected from sodium methoxide and potassium t-butoxide.

In another embodiment, the cyclization agent in step (b) is selected from palladium reagents, such as palladium acetate (monomer or trimer), palladium complexes, and palladium halides, and any mixture thereof. Preferably, the reaction in step (b) is performed in the presence of a base such as sodium acetate, sodium carbonate, triethylamine, and any mixture thereof.

In yet another embodiment, the organic acid in step (c) is selected from acetic acid, trifluoroacetic acid, propionic acid, and any mixture thereof.

In yet another embodiment, the deprotecting agent in step (d) is selected from aqueous hydrobromic acid, aqueous hydrochloric acid, and any mixture thereof.

In yet another embodiment, the difluoromethylating agent in step (c) (ii) is selected from chlorodifluoromethane, sodium chlorodifluoroacetate, and any mixture thereof.

In yet another embodiment, the solvents in the oxidation steps are selected from ethers (e.g., dioxane and tetrahydrofuran), aprotic polar solvents (e.g., dimethylformamide, dimethylsulfoxide, N,N-dimethyl aniline and N-methylpyrrolidine), protic polar solvents (e.g., water, methanol, ethanol, isopropanol and n-butanol), and mixtures thereof.

In yet another embodiment, the oxidizing agents are selected from iodine, potassium iodide, sodium iodide, phenyliodinediacetate, N-hydroxysuccinimide, potassiumperoxomonosulfate, and mixtures thereof.

In yet another embodiment, the oxidizing agents are selected from selenium dioxide, dichlorodicyanoquinone, sodium hypochlorite and tetrabutyl ammoniumsulphate, ozone and silicon dioxide, pyridinium chlorochromate and acetonitrile, pyridinium chlorochromate and acetic acid, ceric ammonium nitrate, laccase diammonium salt of 2,2,azinobis-(3-ethylbenzothiazoline-6-sulfonic acid), and mixtures thereof.

In yet another embodiment, $R_1$ is hydrogen and $R_2$ is 3,5-dichloro-4-pyridinyl. Preferably, P is $CHF_2$.

In yet another embodiment, $R_1$ is hydrogen and $R_2$ is 3,5-dichloro-4-pyridinyl-N-oxide. Preferably, P is $CHF_2$.

Other objects will be set forth in the accompanying detailed description, which follows and in part will be apparent from the description or may be learnt by the practice of the invention. However, it should be understood that the following detailed description are given by way of illustration only since various changes and modification within the scope of the invention will be apparent to those skilled in the art and are included within the scope of this invention.

DETAILED DESCRIPTION OF THE INVENTION

Definitions

The term "alkyl" refers to an optionally substituted straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). In one embodiment, the alkyl chain has one to six carbon atoms. The optional substituents can be, for example, halogens.

The terms "halogen" or "halo" includes fluorine, chlorine, bromine, or iodine.

The term "alkoxy" denotes an alkyl group attached via an oxygen linkage to the rest of the molecule. Representative examples of such groups are $-OCH_3$ and $-OC_2H_5$.

The term "alkoxyalkyl" is used to denote a group comprised of an alkyl group substituted with an alkoxy group, where the alkyl group and alkoxy group are as defined above.

The term "halogenated alkyl" is used to denote a group comprised of an alkyl group substituted with one or more halogen atoms, where the alkyl group is as defined above and the halogen is used to denote fluorine, chlorine, bromine or iodine. Examples of halogenated alkyl groups include, but are not limited to, trifluoromethyl and difluoromethyl.

The term "cycloalkyl" denotes a non-aromatic mono or multicyclic ring system of about 3 to 12 carbon atoms. Non-limiting examples of mono-cyclic ring systems include cyclopropyl, cyclobutyl, cyclopentyl, and cyclohexyl. Non-limiting examples of multicyclic cycloalkyl groups include perhydronaphthyl, adamantyl and norbornyl groups, bridged cyclic groups, and sprirobicyclic groups e.g., spiro(4,4)non-2-yl.

The term "cycloalkylalkyl" refers to a cyclic ring-containing radical having from 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "heterocyclyl" refers to an optionally substituted 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized, and the ring radical may be partially or fully saturated or unsaturated (i.e., heterocyclic or heteroaryl).

The term "aryl" refers to an optionally substituted aromatic radical having 6 to 14 carbon atoms such as phenyl, naphthyl, tetrahydronaphthyl, indanyl, and biphenyl.

The term "heteroaryl" refers to a 5- to 14-membered aromatic heterocyclic ring with one or more heteroatom(s) independently selected from N, O or S, wherein the heteroaryl is a mono, bi or tricyclic ring system.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; salts of chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of the invention with alkyl halides or alkyl sulphates such as MeI and $(Me)_2SO_4$; and salts of non natural amino acids such as D-isomers or substituted amino acids (e.g., guanidine or substituted guanidine wherein the substituents are selected from nitro, amino, alkyl); ammonium or substituted ammonium salts and aluminum salts. Salts may include acid addition salts, where appropriate, such as sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

The term "protecting group" refers to a substituent that is employed to prevent the atom or functional group to which it is attached from undergoing a chemical reaction, while the protecting group remains attached to that atom or functional group of the molecule. By way of example, an "amino-protecting group" is a substituent attached to an amino group that prevents a chemical reaction from occurring on the nitrogen to which it is attached. Suitable amino-protecting groups include, but are not limited to, acetyl, trifluoroacetyl, t-butoxycarbonyl (BOC), benzyloxycarbonyl (CBz) and 9-fluorenylmethylenoxycarbonyl (Fmoc). A "hydroxy-protecting group" refers to a substituent bound to a hydroxy group and prevents the hydroxy functionality from chemical reactivity. Suitable hydroxy-protecting groups include, but are not limited to, acetyl, benzyl, tetrahydropyranyl and silyl. A "carboxy-protecting group" refers to a substituent of the carboxy group that blocks or protects the carboxy functionality from chemical reactivity. Suitable carboxy-protecting groups include, but are not limited to, —$CH_2CH_2SO_2Ph$, cyanoethyl, 2-(trimethylsilyl)ethyl, 2-(trimethyl silyl)ethoxymethyl, 2-(p-toluenesulfonyl)ethyl, 2-(p-nitrophenylsulfenyl)ethyl, 2-(diphenyl phosphino)-ethyl, and nitroethyl. For a general description of protecting groups and their use, see, T. W. Greene, Protective Groups in Organic Synthesis, John Wiley & Sons, New York, 1991.

The term "substituted" refers to one or more substituents selected from hydroxy, halogen, carboxyl, cyano, amino, nitro, oxo (═O), thio (═S), optionally substituted alkyl, optionally substituted alkoxy, optionally substituted alkenyl, optionally substituted alkynyl, optionally substituted aryl, optionally substituted arylalkyl, optionally substituted cycloalkyl, optionally substituted aryl, optionally substituted heteroaryl, optionally substituted heteroarylalkyl, optionally substituted heterocyclic ring, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(═N—N($R^x$)$R^y$), —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yR^z$, —$R^xR^yR^z$, —$R^xCF_3$, —$R^xN$-$R^yC(O)R^z$, —$R^xC(O)OR^y$, —$R^xC(O)NR^xR^z$, —$R^xC(O)R^x$, —$R^xOC(O)R^y$, —$SR^x$, —$SOR^x$, —$SO_2R^x$, —$ONO_2$, wherein $R^x$, $R^y$ and $R^z$ are independently hydrogen, substituted or unsubstituted alkyl, haloalkyl, substituted or unsubstituted arylalkyl, substituted or unsubstituted aryl, substituted or unsubstituted cycloalkyl, substituted or unsubstituted cycloalkylalkyl, substituted or unsubstituted heterocyclic ring, substituted or unsubstituted heterocyclylalkyl, substituted or unsubstituted heteroaryl or substituted or unsubstituted heteroarylalkyl. According to one embodiment, the substituents in the aforementioned "substituted" groups cannot be further substituted.

Below is a process for preparing a compound of formula (6) according to the present invention.

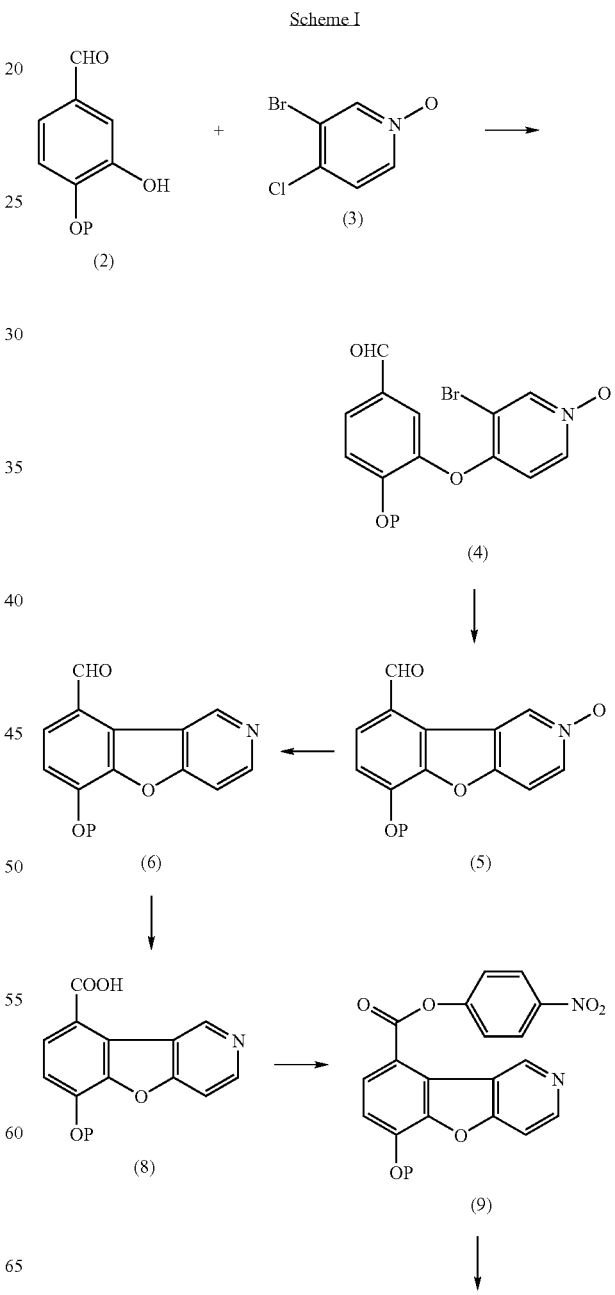

Scheme I

-continued

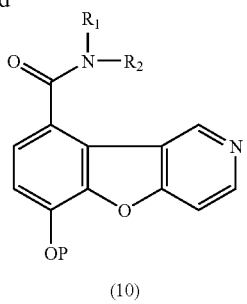

(10)

In scheme I, the compound of formula (2) is reacted with a compound of formula (3) to form a compound of formula (4). The compound of formula (4) is cyclized to form a compound of formula (5). The compound of formula (5) is converted into a compound of formula (6), which is oxidized to form a compound of formula (8). The compound of formula (8) is converted to a compound of formula (10), an N-oxide thereof, or a pharmaceutically acceptable salt thereof. This conversion can be performed by methods known in the art including, for example the method described in WO 2006/064355, which is hereby incorporated by reference.

The compound of formula (2) can be prepared from 3,4-dihydroxy benzaldehyde by processes known in the art including, for example, the methods described in *J. Am. Chem. Soc.*, 100, 3559 (1978), WO 2004/089940 and WO 2006/040652, and U.S. Patent Publication Nos. 2005027129 and 2006135779, all of which are hereby incorporated by reference. The compound of formula (3) can be prepared following the procedures known to a person of ordinary skill in the art including, for example, the method described in *J. Med. Chem.*, 45, 5182-5185 (2002), which is hereby incorporated by reference.

The reaction of a compound of formula (2) with a compound of formula (3) can be carried out in the presence of one or more metal halides or metal hydrides, such as those described above, and optionally in one or more solvents. Preferably, the reaction is performed in the presence of potassium fluoride. The reaction may also be carried out in one or more high boiling solvents such as dimethylsulfoxide, dimethylformamide, N,N-dimethylacetamide, N-methylpyrrolidone, or any mixture thereof. Preferably, the solvent is dimethylsulfoxide or dimethylformamide The cyclization is performed by reacting the compound of formula (4) with one or more cyclizing agents. Suitable cyclizing agents include, but are not limited to, palladium reagents, such as palladium acetate (monomer or trimer), palladium complexes, and palladium halides, and any mixture thereof. The reaction is also preferably performed in the presence of a base such as sodium acetate, sodium carbonate, triethylamine, and any mixture thereof. The cyclization may also be carried out in one or more high boiling solvents, such as dimethylformamide, dimethylsulfoxide, N,N-dimethylaniline, N-methylpyrrolidine or any mixture thereof.

The conversion of the compound of formula (5) to the compound of formula (6) can be performed using metal powder and/or one or more organic acids. Suitable metal powders include, but are not limited to, iron powder, zinc powder and mixtures thereof. Suitable organic acids include, but are not limited to, acetic acid, trifluoroacetic acid, propionic acid, or any mixture thereof. Preferably, the conversion is performed in the presence of acetic acid and iron powder.

The oxidation of a compound of formula (6) to form a compound of formula (8) can be performed by reacting the compound of formula (6) with one or more oxidizing agents optionally in one or more solvents. Suitable oxidizing agents include, but are not limited to, selenium dioxide, dichlorodicyanoquinone, sodium hypochlorite and tetrabutyl ammoniumsulphate, ozone and silicon dioxide, pyridinium chlorochromate and acetonitrile, pyridinium chlorochromate and acetic acid, ceric ammonium nitrate, laccase diammonium salt of 2,2,azinobis-(3-ethylbenzothiazoline-6-sulfonic acid) and mixtures thereof. Suitable solvents include, but are not limited to, ethers (e.g., dioxane and tetrahydrofuran), aprotic polar solvents (e.g., dioxane, dimethylformamide, dimethylsulfoxide, N,N-dimethyl aniline, and N-methylpyrrolidine), protic polar solvents (e.g., water, methanol, ethanol, isopropanol, and n-butanol) or a mixture thereof.

Below is an alternative process for preparing a compound of formula (6) according to the present invention Scheme II

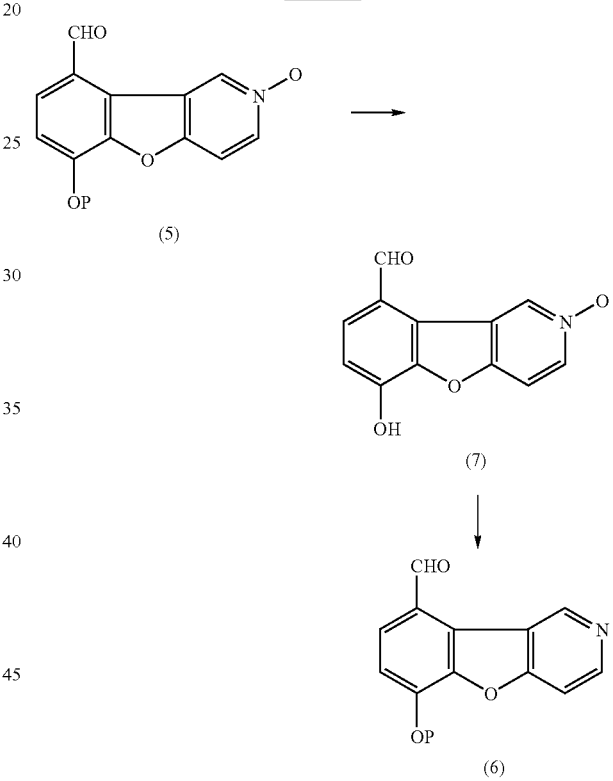

In scheme II, the compound of formula (5) is deprotected to form a compound of formula (7), which is reacted with one or more difluoromethylating agents to form a compound of formula (6), where P is $CHF_2$.

The deprotection of the compound of formula (5) to the compound of formula (7) can be performed by reaction with a deprotecting agent. Suitable deprotecting agents include, but are not limited to, hydrochloric acid (e.g., aqueous hydrochloric acid), hydrobromic acid (e.g., aqueous hydrobromic acid or hydrobromic acid in acetic acid), boron tribromide, aluminium chloride, sodium alkyl or aryl thiolate, tetra-n-butylammonium fluoride and hydrogenating catalysts (e.g., palladium on carbon, rhodium on carbon, platinum black, palladium chloride, platinum oxide, and ruthenium) or a mixture thereof. The reaction may also be carried out in the presence of one or more metal hydroxides. Suitable metal hydroxides include, but are not limited to, alkali metal hydroxides (such as sodium hydroxide, lithium hydroxide or potassium hydroxide), alkaline earth metal hydroxides (such as calcium hydroxide or magnesium hydroxide), and mixtures thereof. Preferably, the conversion is carried out in the presence of aqueous hydrobromic acid and sodium hydroxide.

The conversion of a compound of formula (7) to form a compound of formula (6) can be carried out by reaction with one or more difluoromethylating agents in one or more solvents. Suitable difluoromethylating agents include, but are not limited to, chlorodifluoromethane, sodium chlorodifluoroacetate or a mixture thereof. Suitable solvents include, but are not limited to, ethers (e.g., diethyl ether, tetrahydrofuran and dioxane), aliphatic hydrocarbons (e.g., hexane and heptane), aromatic hydrocarbons (e.g., toluene and xylene), halogenated solvents (e.g., dichloromethane, dibromomethane, chloroform, and carbon tetrachloride), aprotic polar solvents (e.g., dimethylformamide, dimethylsulfoxide, N,N-dimethyl acetamide and N-methylpyrrolidone), protic polar solvents (e.g., methanol, ethanol, isopropanol, butanol and isobutanol), and mixtures thereof.

The present invention also provides a process for preparing a compound of Formula I

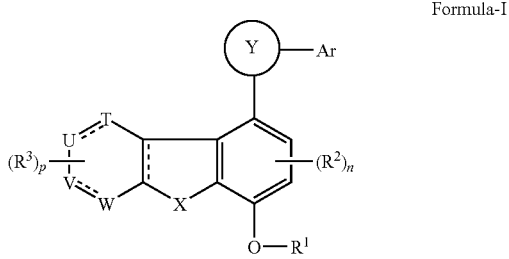

Formula-I an N-oxide thereof, or a pharmaceutical acceptable salt thereof,
wherein $R^1$, $R^2$ and $R^3$ may be the same or different and are independently selected for each occurrence from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, —$NR^5R^6$, —C(=L)-$R^5$, —C(O)—$R^5$, —C(O)O—$R^5$, —C(O)$NR^5R^6$, —S(O)$_m$—$R^5$, —S(O)$_m$—$NR^5R^6$, nitro, —OH, cyano, oxo, formyl, acetyl, halogen, —$OR^5$, —$SR^5$, and protecting groups or when two $R^2$ or two $R^3$ substituents are ortho to each other, they may be joined to a form a 3-7 member optionally substituted saturated or unsaturated cyclic ring, which may optionally include up to two heteroatoms selected from O, $NR^5$ or S;

$R^5$ and $R^6$ may be the same or different and are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, nitro, halo, —OH, cyano, —C(O)—$R^a$, —C(O)O—$R^a$, —C(O)$NR^aR^b$, —S(O)$_m$—$R^a$, —S(O)$_m$—$NR^aR^b$, —C(=$NR^a$)—$R^b$, —C(=$NR^a$)—$NR^aR^b$, —C(=S)—$NR^aR^b$, —C(=S)—$R^a$, —N=C($R^aR^b$), —$NR^aR^b$, —$OR^a$, —$SR^a$, and protecting groups or $R^5$ and $R^6$, when directly bound to the same nitrogen atom, may be joined together to form a 3-7 member optionally substituted saturated or unsaturated cyclic ring, which may optionally include up to two heteroatoms selected from O, $NR^a$ or S;

$R^a$ and $R^b$ may be the same or different and are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, nitro, —OH, cyano, formyl, acetyl, halogen, protecting groups, —C(O)—$R^c$, —C(O)O—$R^c$, —C(O)$NR^aR^c$, —S(O)$_m$—$R^c$, —S(O)$_m$—$NR^cR^d$, —$NR^cR^d$, —$OR^c$, and —$SR^c$;

$R^c$ and $R^d$ may be the same or different and are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, nitro, —OH, cyano, formyl, acetyl, halogen, and protecting groups;

Ar is selected from substituted or unsubstituted aryl, substituted or unsubstituted arylalkyl, substituted or unsubstituted heterocyclic ring, substituted or unsubstituted heteroaryl ring, or substituted or unsubstituted heteroarylalkyl;

L is O, S or $NR^a$, wherein $R^a$ is as defined above;

n is 0-2;

p is 0-4;

T, U, V, and W are each independently selected from C, C=O, N, $NR^a$, O and S, with the proviso that at least one of T, U, V, and W are N, $NR^a$, O, or S, wherein $R^a$ is as defined above;

Dotted lines [----] in the ring represents an optional bond;

X is O, S(O)$_m$ or $NR^a$, wherein $R^a$ is defined as above;

m is 0, 1 or 2;

Y is selected from —C(O)$NR^4$—, —$NR^4SO_2$—, —$SO_2NR^4$— and —$NR^4C(O)$;

$R^4$ is selected from hydrogen, substituted or unsubstituted alkyl, hydroxyl, —$OR^a$ (wherein $R^a$ is as defined above), substituted or unsubstituted aryl, substituted or unsubstituted arylalkyl, substituted or unsubstituted heterocyclic ring, substituted or unsubstituted heteroaryl ring, and substituted or unsubstituted heteroarylalkyl.

The process includes the reaction sequences as depicted in Schemes I and II using the compound of formula (2) with suitable substitution(s) as the starting compound. The substituents in Formula I have the same meaning as defined in PCT Publication No. WO 2006/064355.

In the schemes above, where specific bases, reagents, solvents, oxidizing agents, cyclizing agents etc., are mentioned, it is understood that other bases, reagents, solvents, oxidizing agents, cyclizing agents etc., known to one of ordinary skill in the art may also be used and are therefore envisioned within the scope of this invention. Further, the present invention is illustrated by the following examples. It is understood, however that the invention is not limited by the specific details of the following examples.

EXAMPLES

Example 1

Preparation of 4-difluoromethoxy-3-hydroxy benzaldehyde

To a well stirred suspension of 3,4-dihydroxy benzaldehyde (100 gm) and anhydrous potassium carbonate (120 gm) in dry N,N-dimethylformamide (1.0 lit) was passed chlorodifluoromethane gas for about 30 minutes at about 80-85° C. After an hour another lot of anhydrous potassium carbonate (25.0 gm) was added and stirred for about one and half hours. The third lot of anhydrous potassium carbonate (25.0 gm) was added and stirred for about one and half hours. The reaction mixture was then stirred for about 5-6 hours at an ambient temperature. The reaction mixture was filtered and the filtrate was concentrated under reduced pressure. The residue obtained was diluted with water (500 mL) and extracted with ethyl acetate (3×200 mL). The combined organic layer was dried over anhydrous sodium sulphate and concentrated under reduced pressure. The crude product obtained was purified through silica gel column to give 4-difluoromethoxy-3-hydroxy benzaldehyde.

Yield: 25-30%.

Example 2

Preparation of 3-bromo-4-nitro-pyridine-N-oxide

The synthesis of 3-bromo-4-nitro pyridine-N-oxide is carried out by the method reported in *J. Med. Chem.* 2002, 45, 5182-5185.

Example 3

Preparation of 3-bromo-4-chloro-pyridine-N-oxide

To a well stirred solution of 3-bromo-4-nitro pyridine (12.0 g, 54.794 mmol) in methanol (120 mL) was bubbled dry hydrochloride gas at about 0-5° C. for about 1-2-hours. The reaction mixture was then stirred at ambient temperature for about 6-8 hours. The solvent was evaporated under reduced pressure, the residue obtained was diluted with 20% aqueous solution of sodium hydroxide (100 mL) and extracted with dichloromethane (3×100 mL). The combined organic layer was washed with water and dried over anhydrous sodium sulfate. The solvent was evaporated under reduced pressure to give 3-bromo-4-chloro-pyridine-N-oxide as an off-white crystalline solid.

Yield: >97%, m.p.: 147-149° C.

IR (KBr): —3436, 3078, 3054, 1449, 1414, 1274, 1243, 1150, 1042, 900, 670 cm$^{-1}$.

$^1$H NMR (300 MHz, DMSO-d$_6$): δ 7.71 (d, 1H, J=6.6 Hz), 8.24 (d, 1H, J=5.1 Hz), 8.75 (s, 1H).

Example 4

Preparation of 3-[(3-bromo-pyridin-N-oxide-4-yl) oxy]-4-(difluoromethoxy)benzaldehyde To a well stirred solution of 3,4-difluoromethoxy-3-hydroxy benzaldehyde (2.5 g, 13.3 mmol) in dry dimethylsulfoxide (25 mL) was added potassium fluoride (1.54 g, 26.59 mmol) and the mixture was heated to about 100-110° C. for about 0.5-1 hour. After addition of 3-bromo-4-chloro-pyridine-N-oxide (5.5 g, 26.59 mmol) at ambient temperature, the reaction mixture was heated to about 100-110° C. for about 16-18 hours. The reaction mixture was diluted with water (100 mL) and extracted with dichloromethane (3×50 mL). The combined organic layer was washed with water and dried over anhydrous sodium sulfate. The solvent was evaporated under reduced pressure to give the crude product. It was then purified through silica gel column using methanol in chloroform as an eluent to give 3-[(3-bromo-pyridin-N-oxide-4-yl) oxy]-4-(difluoromethoxy)benzaldehyde as a white solid.

Yield: 65-75%, m.p.: 89-91° C.

IR (KBr): —3444, 3105, 1702, 1590, 1475, 1460, 1426, 1283, 1204, 1115, 1053, 812 cm$^{-1}$.

$^1$H NMR (300 MHz, DMSO-d$_6$): —δ 7.04 (d, 1H, J=7.2 Hz), 7.42 (t, 1H, J=72.6 Hz), 7.64 (d, 1H, J=8.4 Hz), 7.77 (s, 1H), 7.9 (d, 1H, J=8.4 Hz), 8.15 (d, 1H, J=7.5 Hz), 8.73 (s, 1H), 9.95 (s, 1H).

Example 5

Preparation of 6-(difluoromethoxy)[1]benzofuro[3,2-c]pyridine-9-carbaldehyde 2-oxide To a well stirred suspension of 3-[(3-bromo-pyridin-N-oxide-4-yl)oxy]-4-(difluoromethoxy)benzaldehyde (2.5 g, 6.96 mmol) and sodium acetate (1.15 g, 13.92 mmol) in dry dimethylformamide (25 mL) was added palladium acetate trimer (470 mg, 2.08 mmol in ten equal lots of 47 mg) at regular intervals of about 15 minutes at about 110-115° C. The reaction mixture was then cooled to ambient temperature and filtered thorough a celite bed, and the celite bed was washed with dimethylformamide (2×5 mL). The filtrate was concentrated under reduced pressure, and the residue obtained was diluted with water (25 mL) and acidified with glacial acetic acid. The solid obtained was filtered, washed with water and dried to give the crude product. The suspension of crude product in 10% methanol-chloroform (50 mL) was refluxed for about 0.5-1.0 hour. The filtrate obtained after filtration was concentrated to give 6-(difluoromethoxy)[1]benzofuro[3,2-c]pyridine-9-carbaldehyde 2-oxide as a yellow solid.

Yield: 60-70%, m.p.: 215-217° C.

IR (KBr): —3272, 3116, 2997, 2757, 1707, 1658, 1622, 1549, 1369, 1309, 1269, 1256, 1178, 1095, 1082, 857, 817, 799 cm$^{-1}$.

$^1$H NMR (300 MHz, DMSO-d$_6$): —δ 7.69 (t, 1H, J=72.6 Hz), 7.80 (d, 1H, J=8.7 Hz), 8.10 (d, 1H, J=7.2 Hz), 8.27 (d, 1H, J=8.4 Hz), 8.55 (d, 1H, J=7.2 Hz), 9.59 (s, 1H), 10.25 (s, 1H).

Example 6

Preparation of 6-(difluoromethoxy)[1]benzofuro[3,2-c]pyridine-9-carbaldehyde

To a well stirred suspension of 6-(difluoromethoxy)[1]benzofuro[3,2-c]pyridine-9-carbaldehyde 2-oxide (1.0 g, 3.6 mmol) in acetic acid (15 mL) was added iron powder (800 mg, 14.28 mmol) and the mixture was stirred at about 60° C. for about 15-30 minutes. Excess acetic acid was removed under reduced pressure. The residue obtained was diluted with dichloromethane (50 mL) and filtered through a celite bed and the filtrate was washed with water (3×25 mL). The organic layer was dried over anhydrous sodium sulfate and concentrated under reduced pressure to give the crude product. The crude product was purified through a silica gel column using ethyl acetate in dichloromethane as an eluent to give 6-(difluoromethoxy)[1]benzofuro[3,2-c]pyridine-9-carbaldehyde as a white solid.

Yield: 65-75%, m.p.: 215-217° C.

IR (KBr): —3435, 2997, 2343, 1798, 1713, 1686, 1618, 1577, 1501, 1448, 1371, 1341, 1292, 1265, 1196, 1165, 1081, 1022, 802, 772 cm$^{-1}$.

$^1$H NMR (300 MHz, DMSO-d$_6$): —δ 7.68 (d, 1H, J=72.0 Hz), 7.76 (d, 1H, J=8.1 Hz), 8.00 (d, 1H, J=6.0 Hz), 8.24 (d, 1H, J=8.4 Hz), 8.81 (d, 1H, J=8.7 Hz), 10.06 (s, 1H), 10.35 (s, 1H).

Example 7

Preparation of 6-(difluoromethoxy)[1]benzofuro[3,2-c]pyridine-9-carboxylic acid

To a well stirred solution of 6-(difluoromethoxy)[1]benzofuro[3,2-c]pyridine-9-carbaldehyde (500 mg, 1.90 mmol) in acetone (10 mL) was added sulphamic acid (276 mg, 2.85 mmol) at about 10° C. followed by drop wise addition of a solution of sodium chlorite (240 mg, 2.66 mmol) in water (5 mL) at about 0 to 5° C. The mixture was then stirred for about 1-2 hours. Ice cold water (50 mL) was added and the mixture was stirred for about 30 hours. The solid which separated was filtered, washed with water (3×5 mL) and dried at about 60-70° C. to give 6-(difluoromethoxy)[1]benzofuro[3,2-c]pyridine-9-carboxylic acid as a white solid.

Yield: >97%, m.p.: above 250° C.

IR (KBr): —3437, 3191, 1661, 1483, 1282, 1132, 1088, 1055, 892, 838 cm$^{-1}$.

$^1$H NMR (300 MHz, DMSO-d$_6$): —δ 7.58 (d, 1H, J=7.5 Hz), 7.61 (t, 1H, J=71.4 Hz), 7.93 (d, 1H, J=5.7 Hz), 8.14 (d, 1H, J=8.7 Hz), 8.76 (d, 1H, J=6.0 Hz), 10.01 (s, 1H).

Example 8

Preparation of 4-(cyclopentyloxy)-3-hydroxy benzaldehyde

A suspension of 3,4-dihydroxy benzaldehyde (50.0 g, 0.3623 mol), cyclopentyl bromide (135 g, 0.9058 mol) and potassium carbonate (50.0 g, 0.3623 mol) in N,N-dimethylformamide (500 mL) was stirred at about 75-80° C. for about 1.0 hr. 4×12.5 g potassium carbonate was then added after every 1.0 hr. The reaction mixture was cooled to ambient temperature and filtered to remove inorganic materials. The residue obtained after concentration of the filtrate was diluted with toluene (250 mL), and extracted with 5-10% aqueous sodium hydroxide solution (6×50 mL). The combined aqueous layer was acidified to pH about 3 to 5 by 5N aqueous hydrochloric acid solution. The solid which separated was filtered, washed with water and dried to give 4-cyclopentyloxy-3-hydroxy benzaldehyde.

Yield: 50-60 g, m.p. 87-89° C.

IR (Neat): 3433, 2961, 1682, 1594, 1505, 1465, 1424, 1266, 1135, 1032 cm$^{-1}$.

$^1$H NMR (300 MHz, d$_6$-DMSO): δ 1.63-2.03 (m, 8H), 4.86 (m 1H), 6.30 (s, 1H), 7.04 (d, 1H, J=8.4 Hz), 7.41 (brs, 2H), 9.82 (s, 1H).

Example 9

Preparation of 3-[(3-bromo-pyridin-N-oxide-4-yl)oxy]-4-(cyclopentyloxy)benzaldehyde To a well stirred solution of 4-cyclopentyloxy-3-hydroxy benzaldehyde (1.18 g, 5.76 mmol) in dry dimethylformamide (10 mL) was added sodium hydride (253 mg, 6.34 mmol) and the mixture was heated at about 100-110° C. for about 0.5-1 hour. After addition of 3-bromo-4-chloro-pyridine-N-oxide (600 mg, 2.88 mmol) at room temperature, the reaction mixture was heated at about 90-100° C. for about 6-8 hours. The reaction mixture was diluted with water (100 mL) and extracted with dichloromethane (4×25 mL). The combined organic layer was washed with water and dried over anhydrous sodium sulfate. The solvent was evaporated under reduced pressure to give 3-[(3-bromo-pyridin-N-oxide-4-yl)oxy]-4-(cyclopentyloxy)benzaldehyde as a thick yellow oil.

Yield: 80-85%.

IR (KBr): —3402, 2961, 1687, 1601, 1504, 1468, 1427, 1287, 1204, 1113, 976, 816 cm$^{-1}$.

$^1$H NMR (300 MHz, DMSO-d$_6$): —δ 1.32-1.6 (m, 8H), 5.00 (m, 1H), 6.71 (d, 1H, J=7.2 Hz), 7.42 (d, 1H, J=7.8 Hz), 7.78 (s, 1H), 7.87 (d, 1H, J=7.8 Hz), 8.04 (d, 1H, J=8.1 Hz), 8.67 (s, 1H), 9.89 (s, 1H).

Example 10

Preparation of 6-(cyclopentyloxy)[1]benzofuro[3,2-c]pyridine-9-carbaldehyde 2-oxide To a well stirred suspension of 3-[(3-bromo-pyridin-N-oxide-4-yl)oxy]-4-(cyclopentyloxy)benzaldehyde (900 mg, 2.38 mmol) and sodium acetate (393 mg, 4.86 mmol) in dry dimethylformamide (10 mL) was added palladium acetate (160 mg, 0.71 mmol in three equal lots of 53 mg) at regular intervals of 30 minutes at about 120-130° C. The reaction mixture was then cooled to ambient temperature and filtered thorough a celite bed. The celite bed was washed with dimethylformamide (2×5 mL). The filtrate was concentrated under reduced pressure. The residue obtained was diluted with water (25 mL) and acidified with glacial acetic acid. The solid obtained was filtered, washed with water and dried to afford 6-(cyclopentyloxy)[1]benzofuro[3,2-c]pyridine-9-carbaldehyde 2-oxide as a yellow solid.

Yield: 60-70%. m.p.: 181-183"C.

IR (KBr): —3444, 2959, 1714, 1650, 1625, 1283, 1207, 792 cm$^{-1}$.

$^1$H NMR (300 MHz, DMSO-d$_6$): —δ 1.66-2.06 (m, 8H), 5.25 (m, 1H), 7.53 (d, 1H, J=8.4 Hz), 8.00 (d, 1H, J=6.0 Hz), 8.14 (d, 1H, J=8.9 Hz), 8.44 (d, 1H, J=6.6 Hz), 9.56 (s, 1H), 10.11 (s, 1H).

Example 11

Preparation of 6-hydroxy[1]benzofuro[3,2-c]pyridine-9-carbaldehyde-2-oxide

A well stirred suspension of 6-(cyclopentyloxy)[1]benzofuro[3,2-c]pyridine-9-carbaldehyde 2-oxide (200 mg, 0.671 mmol) in 48% aqueous hydrobromic acid (10 mL) was heated to 70-80° C. for 2-3 hours. The reaction mixture was cooled to room temperature and diluted with water (50 mL) and was made alkaline (pH=9-10) by means of a 10% aqueous solution of sodium hydroxide. It was then washed with ethyl acetate (2×25 mL). The aqueous layer was then acidified with acetic acid (pH=4-5) and stirred at 10-15° C. for 30-40 minutes. The solid obtained was filtered and dried to afford 6-hydroxy[1]benzofuro[3,2-c]pyridine-9-carbaldehyde-2-oxide (Yield=80-90%).

IR (KBr): —3439, 2961, 1710, 1662, 1438, 1289, 1210, 1109, 794 cm$^{-1}$.

$^1$H NMR (300 MHz, DMSO-d$_6$): —δ 7.28 (d, 1H, J=8.4 Hz), 7.96 (d, 1H, J=6.3 Hz), 8.03 (d, 1H, J=8.4 Hz), 8.43 (brs, 1H) 9.60 (s, 1H) 10.05 (s, 1H).

Example 12

Preparation of 6-(difluoromethoxy)[1]benzofuro[3,2-c]pyridine-9-carbaldehyde

To a well stirred suspension of 6-hydroxy[1]benzofuro[3,2-c]pyridine-9-carbaldehyde-2-oxide (130 mg, 0.56 mmol) and anhydrous potassium carbonate (235 mg, 1.7 mmol) in N,N-dimethyl formamide (5 mL) was bubbled chlorodifluoromethane gas at 70-80° C. for 3-4 hours. The reaction mixture was cooled to room temperature and filtered through a celite bed to remove inorganic material. The filtrate was concentrated under reduce pressure. The residue obtained was diluted with water (25 mL) and was extracted with ethyl acetate (3×15 mL). The organic layer was dried over anhydrous sodium sulfate and concentrated under reduced pressure to afford the crude product. The crude product was purified through a silica gel column using ethyl acetate in dichloromethane as an eluent to give 6-(difluoromethoxy)[1]benzofuro[3,2-c]pyridine-9-carbaldehyde as a white solid (Yield=60-70%). m.p. —215-217° C.

IR (KBr): —3435, 2997, 2343, 1798, 1713, 1686, 1618, 1577, 1501, 1448, 1371, 1341, 1292, 1265, 1196, 1165, 1081, 1022, 802, 772 cm$^{-1}$.

$^1$H NMR (300 MHz, DMSO-d$_6$): —δ 7.68 (d, 1H, J=72.0 Hz), 7.76 (d, 1H, J=8.1 Hz), 8.00 (d, 1H, J=6.0 Hz), 8.24 (d, 1H, J=8.4 Hz), 8.81 (d, 1H J=8.7 Hz), 10.06 (s, 1H), 10.35 (s, 1H).

We claim:

1. A pharmaceutical composition comprising:
(a) a compound of the formula

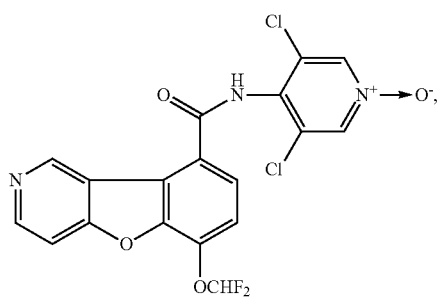

or a pharmaceutically acceptable salt thereof; and
(b) a compound selected from

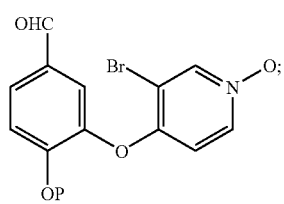
(4)

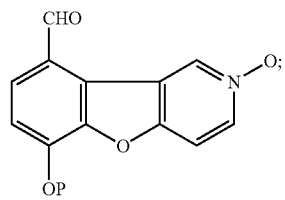
(5)

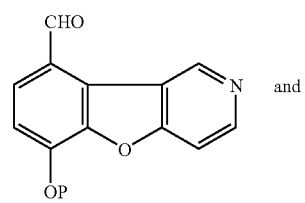
(6)

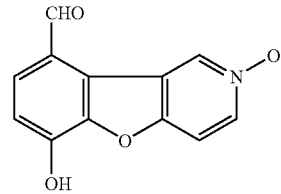
(7)

or a salt thereof, wherein

P is selected from an optionally substituted benzyl, alkyl, halogenated alkyl, cycloalkyl, cycloalkylalkyl, silyl, allyl, propargyl, tetrahydropyran, alkoxyalkyl and silyloxyalkyl, and the compound in component (a) is present in an amount greater than 98% by weight and the compound in component (b) is present in an amount up to 0.1% by weight, based upon 100% total weight of components (a) and (b).

2. A compound selected from:

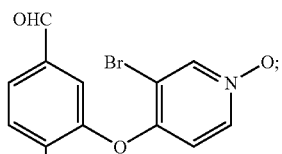
(4)

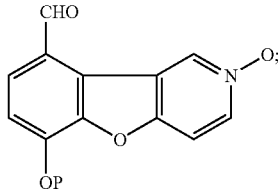
(5)

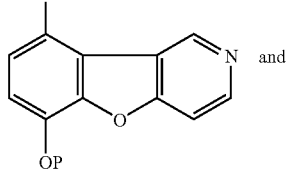
(6)

-continued

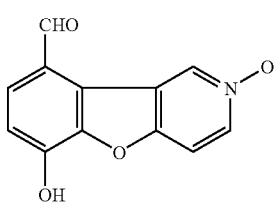
(7)

or a salt thereof,
wherein:
P is selected from an optionally substituted benzyl, alkyl, halogenated alkyl, cycloalkyl, cycloalkylalkyl, silyl, allyl, propargyl, tetrahydropyran, alkoxyalkyl and silyloxyalkyl.

3. A composition comprising:
(a) a compound of the formula

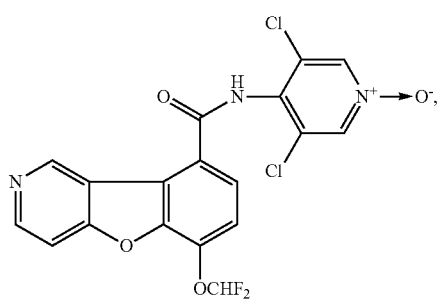

or a pharmaceutically acceptable salt thereof; and
(b) a compound selected from

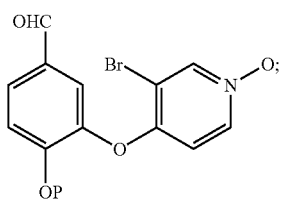
(4)

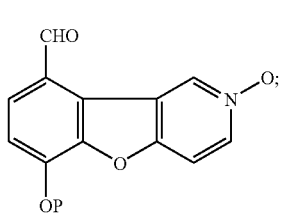
(5)

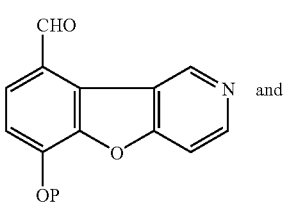
(6)

and

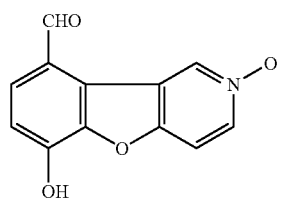
(7)

or a salt thereof, wherein P is selected from an optionally substituted benzyl, alkyl, halogenated alkyl, cycloalkyl, cycloalkylalkyl, silyl, allyl, propargyl, tetrahydropyran, alkoxyalkyl and silyloxyalkyl.

4. The composition of claim 3, wherein the compound in component (a) is present in an amount greater than 98% by weight and the compound in component (b) is present in an amount up to 1% by weight, based upon 100% total weight of components (a) and (b).

5. The composition of claim 3, wherein the compound in component (a) is present in an amount greater than 98% by weight and the compound in component (b) is present in an amount up to 0.1% by weight, based upon 100% total weight of components (a) and (b).

* * * * *